United States Patent
Guan et al.

(10) Patent No.: US 11,123,452 B2
(45) Date of Patent: Sep. 21, 2021

(54) ALKYL CHITOSAN-GRAPHENE OXIDE COMPOSITE SPONGE AND PREPARATION METHOD AND APPLICATION THEREOF

(71) Applicant: Institute of Medical Support Technology, Academy of System Engineering, Academy of Military Science, Tianjin (CN)

(72) Inventors: Jing Guan, Beijing (CN); Jian Yang, Beijing (CN); Ying Zhang, Beijing (CN); Feng Tian, Beijing (CN); Jimin Wu, Beijing (CN); Sheng Ding, Beijing (CN); Zhihong Li, Beijing (CN); Chunlai Wang, Beijing (CN)

(73) Assignee: Institute of Medical Support Technology, Academy of System Engineering, Academy of Military Science, Tianjin (CN)

( * ) Notice: Subject to any disclaimer, the term of this patent is extended or adjusted under 35 U.S.C. 154(b) by 88 days.

(21) Appl. No.: 16/662,774

(22) Filed: Oct. 24, 2019

(65) Prior Publication Data
US 2020/0316248 A1    Oct. 8, 2020

(30) Foreign Application Priority Data
Apr. 4, 2019    (CN) .......................... 201910270233.6

(51) Int. Cl.
*A61L 24/00* (2006.01)
*A61L 24/02* (2006.01)
*A61L 24/08* (2006.01)
*C08B 37/08* (2006.01)

(52) U.S. Cl.
CPC .......... *A61L 24/0036* (2013.01); *A61L 24/02* (2013.01); *A61L 24/08* (2013.01); *C08B 37/003* (2013.01)

(58) Field of Classification Search
CPC .......... C08B 37/003; C08L 5/08; A61L 27/56; A61L 27/303; A61L 24/02; A61L 24/08; A61L 24/0036; A61L 24/0078
USPC .......................................................... 514/55
See application file for complete search history.

(56) References Cited

U.S. PATENT DOCUMENTS 8,790,701 B2 * 7/2014 Rolfes ................. C08B 37/0006
424/488

OTHER PUBLICATIONS

Bao et al, Small 2011, 7(11), 1569-1578.*

* cited by examiner

*Primary Examiner* — Ganapathy Krishnan
(74) *Attorney, Agent, or Firm* — Shackelford, Bowen, McKinley & Norton, LLP; David L. Odom

(57) ABSTRACT

The present invention relates to an alkyl chitosan-graphene oxide composite sponge and preparation method and application thereof. The alkyl chitosan-graphene oxide composite sponge provided by the present invention includes alkyl chitosan and graphene oxide absorbed on the alkyl chitosan, and the adsorbing capacity of the graphene oxide is 3-28 wt. %. In the present invention, alkyl chitosan is used as a matrix to combine graphene oxide and alkyl chitosan; the obtained composite sponge has excellent hemostatic performance and blood absorption capacity. Results of embodiments indicate that the in-vitro whole blood coagulation time is less than 58 s, the hemostasis time of a rabbit femoral artery hemorrhage model is less than 155 s, the hemorrhage mass is less than 5.4 g, and the hemostatic effect is superior to a pure alkyl chitosan sponge or graphene oxide powder when the composite sponge provided by the present invention is used for hemostasis.

12 Claims, 5 Drawing Sheets

ALKYL CHITOSAN-GRAPHENE OXIDE COMPOSITE SPONGE AND PREPARATION METHOD AND APPLICATION THEREOF

This application claims priority to Chinese application number 201910270233.6, filed Apr. 4, 2019, with a title of ALKYL CHITOSAN-GRAPHENE OXIDE COMPOSITE SPONGE AND PREPARATION METHOD AND APPLICATION THEREOF. The above-mentioned patent application is incorporated herein by reference in its entirety.

TECHNICAL FIELD

The present invention belongs to the technical field of medical materials, and specifically relates to an alkyl chitosan-graphene oxide composite sponge and preparation method and application thereof.

BACKGROUND

Excessive hemorrhage is one of the major reasons to cause the death of the people on the battlefield and in accidents, therefore, to design and develop a safe and efficient hemostatic material has been always one of the focused issues.

Chitosan is a kind of positively-charged natural polymer, and featured by good biocompatibility, mucosa adhesion, antibacterial property, hemostasis, etc., but its hemostatic effect is unstable to acute massive bleeding wounds, therefore, it is necessary to modify chitosan materials, thus further improving its hemostatic performance Researches show that a certain amount of alkyl groups grafted onto chitosan aminos could effectively improve the hemostatic performance of chitosan, while the blood absorption performance of the alkyl-grafted chitosan is inferior to the non-grafted chitosan.

SUMMARY

An objective of the present invention is to provide an alkyl chitosan-graphene oxide composite sponge; the composite sponge provided by the present invention both has excellent hemostatic and blood absorption performances, and it is suitable as a medical hemostatic material.

To achieve the above purpose, the present invention provides the following technical solutions.

The present invention provides an alkyl chitosan-graphene oxide composite sponge, including alkyl chitosan and graphene oxide absorbed on the alkyl chitosan, where the adsorbing capacity of the graphene oxide is 3-28 wt. %.

Preferably, the alkyl chitosan-graphene oxide composite sponge has pores, and the porosity is 48-78%; the specific surface area of the alkyl chitosan-graphene oxide composite sponge is $\geq 100$ $m^2/g$.

Preferably, the degree of alkyl substitution of the alkyl chitosan is 3-35%.

Preferably, the carbon chain of the grafted alkyl in the alkyl chitosan is C6-C18.

The present invention provides a preparation method of the above alkyl chitosan-graphene oxide composite sponge, including the following steps of:

(1) mixing a chitosan solution with aldehyde compounds, then adding a reducing agent to obtain alkyl chitosan after reaction;

(2) mixing the alkyl chitosan with acetic acid, graphene oxide and water, then freeze-drying an obtained mixed liquor to obtain an alkyl chitosan-graphene oxide composite sponge.

Preferably, in the step (1), the chitosan solution includes chitosan, acetic acid, ethyl alcohol and water, and the mass ratio of the chitosan to water is 1:(80-120);

the mass ratio of the acetic acid to water is (0.8-1.2):100;
the volume ratio of the ethyl alcohol to water is (70-80):200.

Preferably, in the step (2), the dosage ratio of the alkyl chitosan to acetic acid is 0.1 g:(0.08-0.15) mL.

Preferably, in the step (1), the molar ratio of the aldehyde compounds to aminos in chitosan is (0.3-1.5):1.

Preferably, the freeze drying temperature is −75 to −80° C., and the time is 45-50 h.

The present invention provides an application of the above alkyl chitosan-graphene oxide composite sponge or an alkyl chitosan-graphene oxide composite sponge prepared by the above preparation method as a medical hemostatic material.

The alkyl chitosan-graphene oxide composite sponge provided by the present invention includes alkyl chitosan and graphene oxide absorbed on the alkyl chitosan, and the adsorbing capacity of the graphene oxide is 3-28 wt. %. In the present invention, alkyl chitosan is used as a matrix to form a sponge material having pore structures by means of the recombination between graphene oxide and alkyl chitosan; the obtained composite sponge is applied in hemostasis, and its blood absorption capacity enhances significantly, hemostasis time shortens obviously and hemorrhage mass decreases significantly relative to conventional hemostatic materials. Results of embodiments have indicated that the in-vitro whole blood coagulation time is less than 58 s, the hemostasis time of a rabbit femoral artery hemorrhage model is less than 155 s, the hemorrhage mass is less than 5.4 g, and the hemostatic effect is superior to a pure alkyl chitosan sponge or graphene oxide powder.

BRIEF DESCRIPTION OF THE DRAWINGS

In FIGS. 1-8 and text below, CS represents chitosan, AC represents alkyl chitosan, AC6a, AC6b and AC6c represent N-hexyl chitosan powder (corresponding to the products of step 1 in embodiments 1-3 respectively), AC12a, AC12b and AC12c represent N-dodecyl chitosan powder (corresponding to the products of step 1 in embodiments 4-6 respectively), AC18a, AC18b, AC18c represent N-octadecyl chitosan powder (corresponding to the products of step 1 in embodiments 7-9 respectively), ACGS0 represents dodecyl chitosan sponge, ACGS5 represents a dodecyl chitosan-graphene oxide composite sponge prepared in embodiment 4, ACGS10 represents a dodecyl chitosan-graphene oxide composite sponge prepared in embodiment 10, ACGS20 represents dodecyl chitosan-graphene oxide composite sponge prepared in embodiment 11, Blank represents a blank sample, Gauze represents medical gauze, Celox represents commercially available chitosan hemostatic powder, GO represents graphene oxide powder.

DETAILED DESCRIPTION

Figure 1:
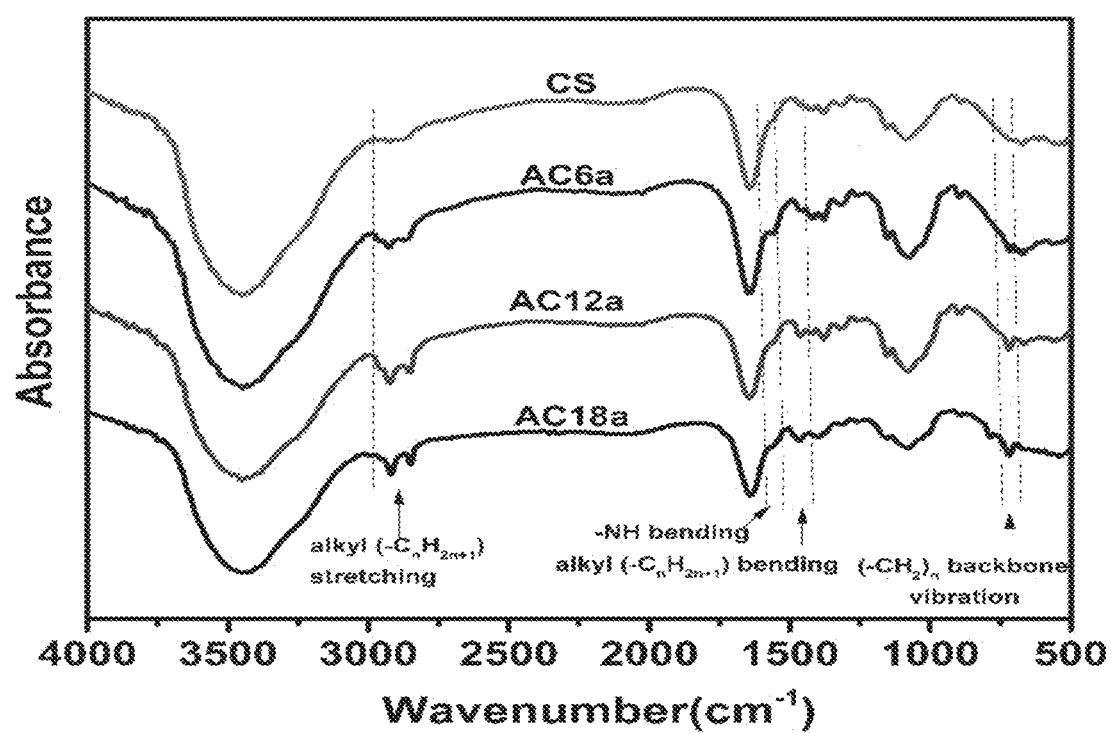
FIG. 1 is an FTIR contrast diagram between chitosan powder and alkyl chitosan powder.

In the following detailed embodiments, unless otherwise described specifically, all the reagents used are the familiar products available in the market to those skilled in the art.

The present invention provides an alkyl chitosan-graphene oxide composite sponge, including alkyl chitosan and graphene oxide absorbed on the alkyl chitosan, and the adsorbing capacity of the graphene oxide is 3-28 wt. %.

Alkyl chitosan is used as a matrix of the alkyl chitosan-graphene oxide composite sponge provided by the present invention. In the present invention, the carbon chain of the grafted alkyl in the alkyl chitosan is preferably C6-C18, more preferably C8-C14, further preferably C10-C12. In detailed implementation process of the present invention, the alkyl chitosan preferably includes one or more of N-hexyl chitosan (AC6 for short), N-dodecyl chitosan (AC12 for short) and N-octadecyl chitosan (AC18 for short), more preferably AC6, AC12 or AC18, further preferably AC12. In the present invention, degree of substitution is counted by a ratio of the number of aminos in the grafted alkyl to the sum of aminos in chitosan, the degree of alkyl substitution of the alkyl chitosan is preferably 3-35%, and specifically, the degree of alkyl substitution is preferably 15-33%, more preferably 25-32% when the alkyl chitosan is AC6;

the degree of alkyl substitution is preferably 12-33%, more preferably 16-32% when the alkyl chitosan is AC12;

the degree of alkyl substitution is preferably 10-25%, more preferably 18-22% when the alkyl chitosan is AC18.

In the present invention, the above structure of alkyl chitosan is preferably used as a matrix, which is capable of providing a basis to obtain a hemostatic sponge having excellent hemostatic performance.

The alkyl chitosan-graphene oxide composite sponge includes graphene oxide absorbed on alkyl chitosan. In the present invention, the alkyl chitosan carries positive charge, graphene oxide carries negative charge, and the both two bond with each other by electrostatic adsorption and intermolecular hydrogen bonding, which improves the stability of material performance. In the present invention, the adsorbing capacity of the graphene oxide is preferably 3-28 wt. %, more preferably 12-25 wt. %, further preferably 15-23 wt. %. In the present invention, the content of the graphene oxide may be used as a modifier, which not only keeps the hemostasis of alkyl chitosan at a higher level, but also improves the blood absorption capacity of composite sponge.

The alkyl chitosan-graphene oxide composite sponge provided by the present invention has pores, diameter of the pores is preferably 20-40 μm, more preferably 25-35 μm; porosity is preferably 48-78%, more preferably 60-75%; specific surface area is preferably ≥100 $m^2$/g, more preferably 110-125 $m^2$/g. In the present invention, the pore structure of the alkyl chitosan-graphene oxide composite sponge may improve the blood absorption capacity of the material.

The present invention further provides a preparation method of the alkyl chitosan-graphene oxide composite sponge in the above technical solution, including the following steps of:

(1) mixing a chitosan solution with aldehyde compounds, then adding a reducing agent to obtain alkyl chitosan after reaction;

(2) mixing the alkyl chitosan with acetic acid, graphene oxide and water, then freeze-drying an obtained mixed liquor to obtain an alkyl chitosan-graphene oxide composite sponge.

The chitosan solution is mixed with aldehyde compounds and the reducing agent is added for reaction to obtain the alkyl chitosan in the present invention. In the present invention, the chitosan solution includes chitosan, acetic acid, ethyl alcohol and water, where:

the mass ratio of the chitosan to water is preferably 1:(80-120), more preferably 1:100;

the mass ratio of the acetic acid to water is preferably (0.8-1.2):100, more preferably (0.9-1.0):100;

the volume ratio of the ethyl alcohol to water is (70-80): 200, more preferably 75:200.

In the present invention, acetic acid, ethyl alcohol and water are preferably used to prepare the chitosan solution, which may promote the dissolving of chitosan into water and may bring advantages to the follow-up alkylation reaction.

In the present invention, the preparation method of the chitosan solution is preferably as follows: acetic acid and water are mixed to obtain the aqueous acetic acid; chitosan and the aqueous acetic acid are mixed, then ethyl alcohol is added to obtain the chitosan solution. In the present invention, the above mixing process is preferably conducted in stirring conditions, the stirring rate is preferably (200-500) r/min, more preferably (350-400) r/min; during the mixing process of acetic acid and water, the stirring time is preferably 5 min; during the mixing process of chitosan and aqueous acetic acid, the stirring time is preferably 90 min; after adding ethyl alcohol, the stirring time is preferably 0.8-1.5 h, more preferably 1 h.

In the present invention, C-chain structures of the aldehyde compounds are consistent with the alkyl C-chain structures in the alkyl chitosan, for example, the corresponding aldehyde compound of AC6 is hexaldehyde, the corresponding aldehyde compound of AC12 is lauraldehyde, and the corresponding aldehyde compound of AC18 is stearaldehyde. In the present invention, dosage of the aldehyde compounds is preferably determined according to the number of aminos on chitosan molecular chains and the required degree of substitution, moreover, aldehyde compounds are added according to 2.4-7.2 times the dosage required by the degree of substitution.

In detailed embodiments of the present invention, counted by the sum of aminos in chitosan, the molar ratio of the aldehyde compounds to aminos in chitosan is preferably (0.3-1.5):1, more preferably (0.6-1.0):1.

In the present invention, after the chitosan solution is mixed with aldehyde compounds, the mixed liquor is regulated to be weak acid, the pH corresponding to the weak acid is preferably 4-6, more preferably 4.5-5.5; and in the present, the reagent for regulating the pH of the mixed liquor is preferably NaOH.

In the present invention, after the chitosan solution is mixed with aldehyde compounds, a reducing agent is added to the mixed material for reaction to obtain alkyl chitosan. In the present invention, the reducing agent is preferably added to the mixed material in stirring conditions; the reducing agent is preferably added in a solid form; the molar ratio of the addition of the reducing agent to formyl groups in the aldehyde compounds is (2-3):1, more preferably 3:1. In the present invention, the reducing agent preferably includes sodium borohydride or sodium cyanoborohydride, more preferably sodium cyanoborohydride.

In the present invention, alkylation and reduction reactions are conducted among chitosan, aldehyde compounds and reducing agent in the mixed system, then alkyl chitosan is obtained.

In the present invention, the system after reaction is preferably regulated to be alkaline, and the pH of the alkaline material obtained after regulation is preferably 9-11, more preferably 9.5-10; the reagent for regulating pH is preferably sodium hydroxide solution, and the concentration of the sodium hydroxide solution is preferably 8-15 wt. %, more preferably 10-12 wt. %.

There are precipitates in the system after reaction upon that the system after reaction is regulated to be alkaline, in the present invention, the precipitates are preferably collected by filtering or centrifuging, then washed by ethanol solution and water to remove impurities, thus obtaining higher-purity alkyl chitosan. In the present invention, the ethanol solution for washing preferably includes the ethanol aqueous solution whose volume fraction is respectively 50%, 75% and 100%. In the present invention, the precipitates are soaked into the ethanol aqueous solution during washing process to completely remove unreacted aldehyde compounds. In the present invention, the material obtained after washing is preferably frozen-dried to remove the residual deionized water from washing and to obtain the dry alkyl chitosan; the obtained alkyl chitosan is powdered material. In the present invention, the washed material is preferably cooled before freeze drying, the cooling temperature is preferably −24 to −18° C., the cooling time is preferably 6-10 h; in the present invention, after cooling, the cooled material is frozen-dried, the freeze drying temperature is preferably −75 to −80° C., and the time is preferably 22-24 h.

In the present invention, after obtaining alkyl chitosan, the alkyl chitosan is mixed with acetic acid, graphene oxide and water, and then the obtained mixed liquor is frozen-dried to obtain the alkyl chitosan-graphene oxide composite sponge. In the present invention, the dosage of components in the mixed liquor satisfies the following requirements:

the dosage ratio of alkyl chitosan to acetic acid is preferably 0.1 g:(0.08-0.15) mL, more preferably 0.1 g:(0.09-0.12) mL, further preferably 0.1 g:0.1 mL;

the mass ratio of alkyl chitosan to graphene oxide is preferably 0.1 g: (3-28) mg, more preferably 0.1 g: (12-25) mg, further preferably 0.1 g:(15-23) mg;

the dosage ratio of alkyl chitosan to water is preferably 0.1 g:(18-25) mL, more preferably 0.1 g:(20-23) mL, further preferably 0.1 g:20 mL.

In the present invention, the mixed liquor is preferably prepared by the following method: an ultrasonic mixing is conducted to the mixture of graphene oxide and water to obtain a graphene oxide dispersion liquid, then acetic acid and alkyl chitosan are successively added to the graphene oxide dispersion liquid for stirring, then the mixed liquor is obtained. In the present invention, the ultrasonic power is preferably 150-210 W, more preferably 170-190 W; the ultrasonic time is preferably 20-90 min, more preferably 50-70 min; the stirring rate is preferably 100-300 r/min, more preferably 180-220 r/min; after adding acetic acid, the stirring time is preferably 10-20 min, more preferably 15 min; after adding alkyl chitosan, the stirring time is preferably 10-15 h, more preferably 10-12 h.

In the present invention, the mixed liquor is placed in a vessel after obtaining, and then the vessel containing the mixed liquor is frozen-dried. In the present invention, before freeze drying, the vessel containing the mixed liquor is placed in a vacuum drying oven for degassing, during degassing process, the temperature of the vacuum drying oven is preferably 25-35° C., more preferably 30° C.; the vacuum degree is preferably −0.6 to −1.0 bar.

In the present invention, after degassing, the obtained material is frozen-dried, and the freeze drying temperature is preferably −75 to −80° C., and the time is preferably 45-50 h. In the present invention, solvent is preferably removed by a freeze drying way to sublimate ice crystal, thus obtaining the composite sponge having a pore structure.

The present invention further provides an application of the alkyl chitosan-graphene oxide composite sponge of the above technical solution or the alkyl chitosan-graphene oxide composite sponge prepared by the preparation method of the above technical solution as a medical hemostatic material. There is no special requirement to the specific way of the application as long as a way familiar to those skilled in the art is applied in the present invention available.

To further describe the present invention, the alkyl chitosan-graphene oxide composite sponge and preparation method and application thereof provided by the present invention will be described specifically with reference to figures and embodiments, but these figures and embodiments shall be not construed as limiting the protection scope of the present invention.

Embodiment 1

(1) 2 g CS was dissolved into a 200 mL of 1% glacial aqueous acetic acid and stirred at room temperature to be fully dissolved, then 75 mL of absolute ethyl alcohol was added for continuously stirring for 1 h. A certain amount of hexaldehyde (the mole number of chitosan aminos: the mole number of hexaldehyde=1:0.8) was added and its pH was regulated to 5.1 for fully stirring for 4 h, then sodium cyanoborohydride (the molar ratio of formyl group and sodium cyanoborohydride=1:3) was added. PH was regulated by 10 wt. % NaOH solution to 10 after full reaction for 4 h. Precipitates were collected, fully soaked and washed by 50%, 75% and 100% ethanol aqueous solution to remove unreacted alkyl aldehyde, afterwards, products were washed by deionized water to be neutral. The products were frozen at −20° C. over the night (8 h), and frozen-dried (−80° C., 24 h) to obtain final products: AC6 powder with about 32% degree of substitution, named as AC6a;

(2) 5 mg GO was put into 20 mL of deionized water for ultrasonic dispersion for 30 min to form a uniform GO/H$_2$O dispersion liquid; 0.1 mL of glacial acetic acid was added for magnetic stirring for 15 min to form a glacial aqueous acetic acid with 0.5% uniform volume fraction, then 0.1 g AC6a was added for magnetic stirring for 12 h. The mixed liquor was poured into a 6-pore plate, and put in a 30° C. vacuum drying oven to remove bubbles in the solution, and finally, the solution was frozen-dried to obtain a cylindrical alkyl chitosan-graphene oxide composite sponge.

Embodiments 2-9

The alkyl chitosan-graphene oxide composite sponge was prepared according to the way of embodiment 1, the composition or dosage of the aldehyde compounds used was different;

Additionally, in embodiment 4, an alkyl chitosan sponge was further prepared excepting for the preparation of a composite sponge; the method was the same as the preparation method of the composite sponge, the difference was that graphene oxide was not added in step (2), and the rest was conducted according to steps (1) and (2). The components and dosage of embodiments 2-9 were specifically shown in table 1.

Figure 2:
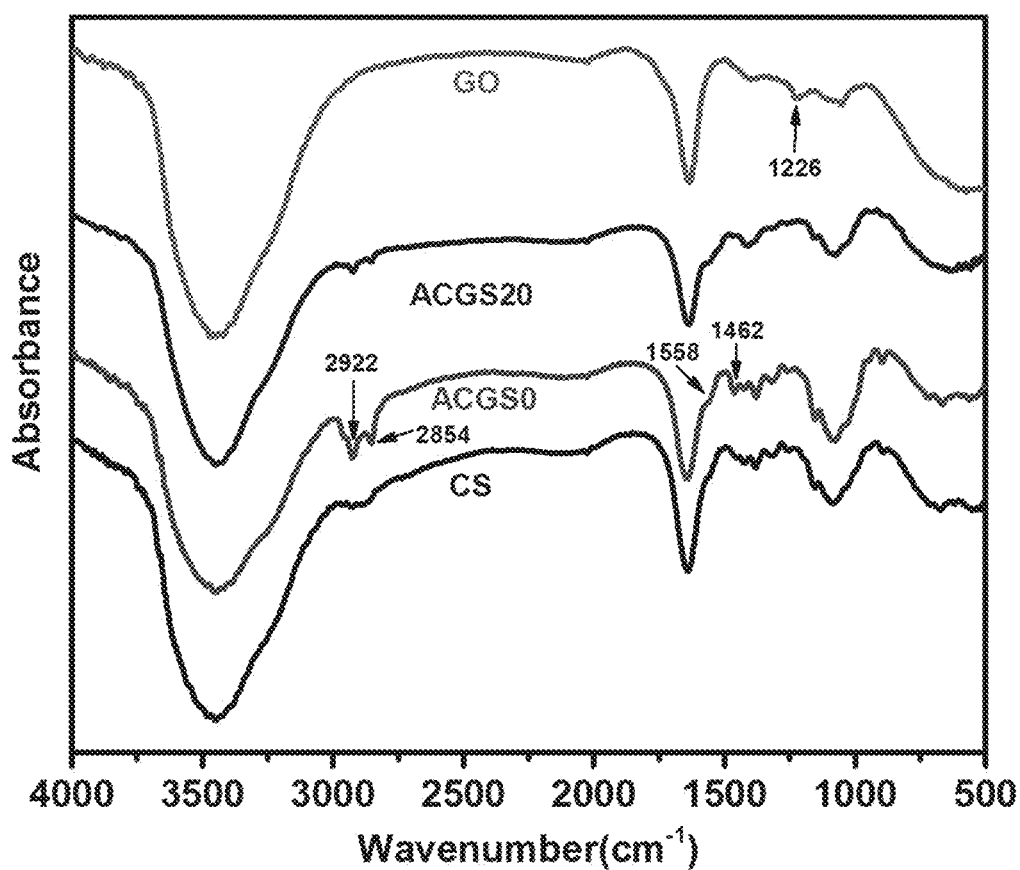
FIG. 2 is an FTIR contrast diagram among graphene oxide powder, dodecyl chitosan-graphene oxide composite sponge, dodecyl chitosan sponge and chitosan powder.

A Tensor 37 infrared spectrometer produced by Newton company was used to characterize the products obtained in embodiments 1-9, results were shown in FIGS. 1 and 2. FIG. 1 is an FTIR contrast diagram between chitosan powder and alkyl chitosan powder, the figure shows that products —CH$_3$ stretching vibration peak (2900-3000 cm$^{-1}$), —CH$_2$ stretching vibration peak (2800-2900 cm$^{-1}$), alkyl bending vibration absorption peak (1440 cm$^{-1}$) and —CH$_2$ framework vibration peak (720 cm$^{-1}$) are obviously enhanced, moreover, with the increase of the alkyl chain length, the absorption peak strengthens; enhancement of the —NH bending peak (1560 cm$^{-1}$) indicates that hexyl, dodecyl and octadecyl have been successfully grafted on CS aminos, and the obtained precipitates are alkyl chitosan. FIG. 2 is an FTIR contrast diagram among graphene oxide powder, dodecyl chitosan-graphene oxide composite sponge, dodecyl chitosan sponge and chitosan powder, and the spectrum shows that the characteristic peak of alkyl chitosan sponge is embodied in a spectrogram of the alkyl chitosan-graphene oxide composite sponge, indicating that the addition of graphene oxide does not break the chemical structure of alkyl chitosan; but the absorption peak (1226 cm$^{-1}$) of epoxy groups of graphene oxide disappears in the spectrogram, indicating that there is certain chemical interaction between alkyl chitosan and graphene oxide besides the interaction of hydrogen bonds and charges when alkyl chitosan and graphene oxide are combined.

A Vario EL/microcube elemental analyzer produced by Elementar company was used to test the content of elements C and N in AC, and the degree of alkyl substitution of AC was calculated, its test results were shown in table 1.

TABLE 1

The content and degree of alkyl substitution of elements C and N of alkyl chitosan in embodiments 1-9

| Embodiment | Aldehyde | Symbol | Amino/Aldehyde (mol:mol) | C (%) | N (%) | SD (%) |
|---|---|---|---|---|---|---|
| 1 | Hexaldehyde | AC6a | 1:0.8 | 44.42 ± 1.11 | 6.33 ± 0.35 | 32.02 ± 0.43 |
| 2 | Hexaldehyde | AC6b | 1:0.6 | 42.37 ± 1.56 | 6.44 ± 0.16 | 24.58 ± 0.95 |
| 3 | Hexaldehyde | AC6c | 1:0.3 | 40.40 ± 0.13 | 7.15 ± 0.84 | 5.53 ± 0.58 |
| 4 | Lauraldehyde | AC12a | 1:0.8 | 49.71 ± 1.59 | 5.69 ± 0.28 | 32.69 ± 0.86 |
| 5 | Lauraldehyde | AC12b | 1:0.5 | 44.27 ± 2.18 | 6.14 ± 0.33 | 17.99 ± 0.75 |
| 6 | Lauraldehyde | AC12c | 1:0.3 | 41.26 ± 1.12 | 6.71 ± 0.40 | 7.57 ± 0.37 |
| 7 | Stearaldehyde | AC18a | 1:1.2 | 51.48 ± 2.01 | 5.13 ± 0.37 | 30.27 ± 0.79 |
| 8 | Stearaldehyde | AC18b | 1:0.6 | 47.64 ± 1.77 | 5.73 ± 0.29 | 19.15 ± 0.63 |
| 9 | Stearaldehyde | AC18c | 1:0.3 | 41.90 ± 1.89 | 6.97 ± 0.42 | 4.18 ± 0.57 |

In table 1, the numbers 6, 12 or 18 in the symbol respectively represent the number of carbon chains of alkyl; a, b and c respectively represent the level of the degree of substitution, a represents high degree of substitution, b represents the moderate, c represents a lowest degree of substitution, SD represents degree of substitution.

It can be seen from the test results of table 1 that the dosage adjustment of aldehyde compounds may change the degree of alkyl substitution, and alkyl chitosan may be optimized and designed based upon this.

Embodiments 10-11

The alkyl chitosan-graphene oxide composite sponge was prepared according to the way of Embodiment 4, the difference lies in the dosage of graphene oxide, as shown in table 2 specifically.

The specific surface area of the obtained products was tested by a methylene blue (MB) dye absorption experiment, and test results were shown in table 2;

The porosity of the dodecyl chitosan-graphene oxide composite sponge was tested by an alcohol absorption method, and the specific method was as follows: same volume (diameter-1.5 cm, height-1 cm) of samples ACGS0 and ACGS20 were weighed respectively and denoted as $m_0$. Samples were soaked into absolute ethyl alcohol, weighed and denoted as $m_1$ when saturation, 6 parallel samples were set to each sample, and the porosity was calculated according to the following formula: porosity=$(m_1-m_0)/(\rho V)$, of which, $\rho$ represents the density of absolute ethyl alcohol, V represents the initial volume of ACGS, and test results were shown in table 2.

TABLE 2

Raw materials dosage and structure parameters of the obtained products in embodiments 4, 10 and 11

| Embodiment | Alkyl chitosan | Graphene oxide (mg) | Specific surface area (m$^2$/g) | Porosity (%) | Pore diameter (μm) |
|---|---|---|---|---|---|
| 4  | AC12a | 0   | 116.76 ± 6.53 | 61.84 ± 4.03 | 20.23 ± 5.29 |
| 4  | AC12a | 5   | 120.09 ± 6.90 | 65.11 ± 2.19 | 27.86 ± 6.39 |
| 10 | AC12a | 10  | 120.32 ± 5.43 | 70.69 ± 3.11 | 31.62 ± 4.76 |
| 11 | AC12a | 20  | 122.28 ± 2.6  | 75.82 ± 1.53 | 34.26 ± 5.60 |
|    | CS    | 0   | 99.43 ± 6.81  | 57.49 ± 4.97 | 18.19 ± 6.01 |
|    | GO    | 100 | 788 ± 1 6.63  | 88.35 ± 8.48 | 47.62 ± 8.75 |

It can be seen from the test results of table 2 that compared with chitosan, the alkyl chitosan-graphene oxide composite sponge obtained from the present invention has higher specific surface area and porosity, which provides a basis for the improvement of hemostasis and blood absorption capacity of the composite sponge.

The alkyl chitosan sponge and alkyl chitosan-graphene oxide composite sponge were prepared into strips (length 50 mm×width 10 mm×height 2 mm), and a universal testing machine was used to test its mechanical property by 10 mm/min stretching velocity at room temperature to obtain tensile strength and elongation at break, 6 sets of parallel samples were set for each sample. The tensile strength of ACGS0 obtained by embodiment 4 is 0.07±0.01 MPa, and the elongation at break is 19.55±1.77%; the tensile strength of ACGS20 obtained by embodiment 11 is 0.11±0.01 MPa, and the elongation at break is 18.88±0.035%. It indicates that the tensile strength of the composite sponge significantly enhances, which strengthens the mechanical stability of materials during hemostasis process, and is beneficial to preventing wound hemorrhage more effectively.

Figure 3:
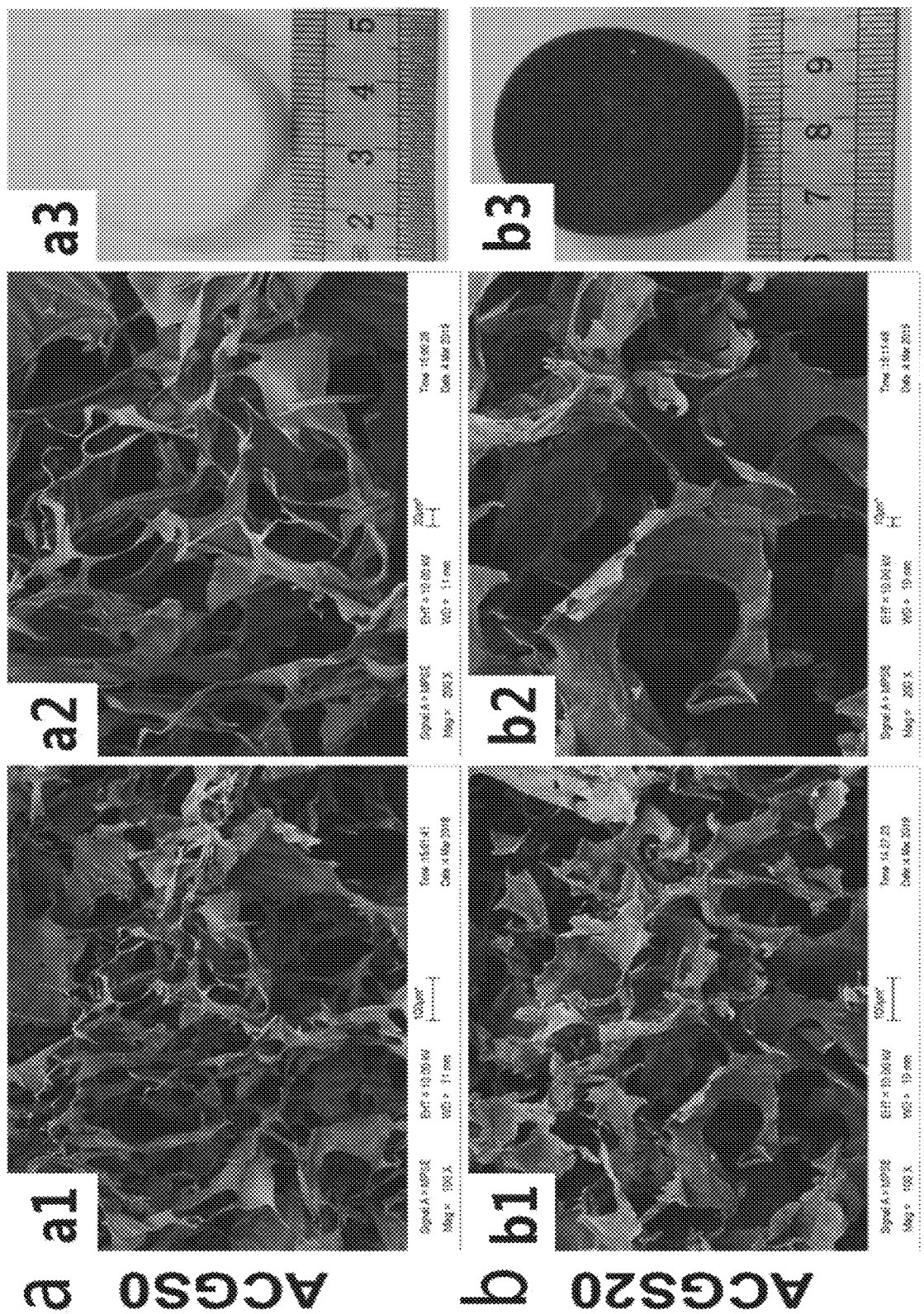
FIG. 3 is an SEM diagram of dodecyl chitosan-graphene oxide composite sponge.

The microstructure and morphology of the alkyl chitosan-graphene oxide composite sponge obtained from embodiments were characterized by a scanning electron microscope, where the characterization results of ACGS0 and ACGS20 are shown in FIG. 3. In FIG. 3, (a) is SEM diagrams of low power (a1) and high power (a2) of ACGS0 and pictures of real products (a3); (b) is SEM diagrams of low power (b1) and high power (b2) of ACGS20 and pictures of real products (b3); it can be seen from the test results that ACGS0 and ACGS20 have porous structures, compared with ACGS0, ACGS20 has a more fluffy pore structure and larger diameter, which contributes to plasma absorption and the concentration of erythrocyte, blood platelets, plasma proteins and various blood coagulation factors, thus facilitating blood coagulation. The test results of other embodiments were consistent with the above conclusion, and moreover, the composite sponge having loose porous structures was obtained as well.

Figure 4:
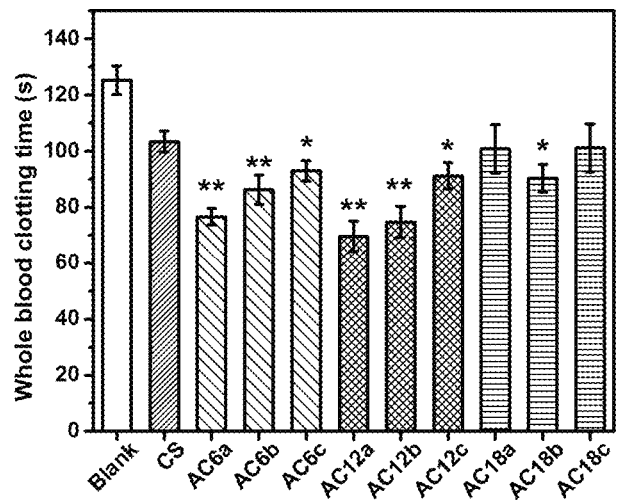
FIG. 4 is a contrast diagram showing the test results statistics of in-vitro whole blood coagulation time among a blank sample, chitosan powder and alkyl chitosan powder.

The whole blood coagulation time of the obtained products was tested by the below method: 20 mg samples were added into a 10 mL of glass test tube for incubation in a thermostatic water bath at 37° C. for 3 min, then 1 mL of anti-coagulating whole blood was added for continuous incubation for 3 min, afterwards, 775 μL of 0.025 mol/L CaCl$_2$ solution was added to the test tube. The test tube was inclined every other 15 s at 37° C. and observed whether blood flows till the blood didn't flow any longer when the test tube was inclined 90°, at this time, it was recognized as blood coagulation, then the coagulation time was recorded. The anti-coagulating whole blood without samples was served as a Blank group, and each of samples was repeatedly tested for 3 times. In-vitro blood coagulation test was conducted to AC powders obtained by embodiments 1-9, and the test results were shown in FIG. 4. It can be seen from FIG. 4 that compared with CS, the in-vitro blood coagulation time of the AC obtained from the present invention shortens (see FIG. 4). The in-vitro blood coagulation time of AC12a is shortest, about 70 s.

The blood absorption capacity of the composite sponge was evaluated by testing the material's absorption rate to whole blood within 1 min, and the method was as follows: blood was sampled from the heart of a 2.5-3 kg of New Zealand rabbit, 3.8 wt % sodium citrate was mixed with the fresh blood according to a ratio of 1:9 to obtain anti-coagulating whole blood. The weighed ACGS0, ACGS20 and gauze (m$_2$) were respectively soaked into the anti-coagulating whole blood, and samples were taken out after blood was absorbed at 5 s, 10 s, 20 s, 30 s, 40 s and 60 s respectively and rapidly, redundant blood on the surface was absorbed by filter paper and weighed, denoted as m$_3$. 6 parallel samples were set for each sample. The blood absorption capacity was calculated by the below formula: absorption multiple=(m$_3$−m$_2$)/m$_2$. The calculating results were shown in FIG. 5.

Figure 5:
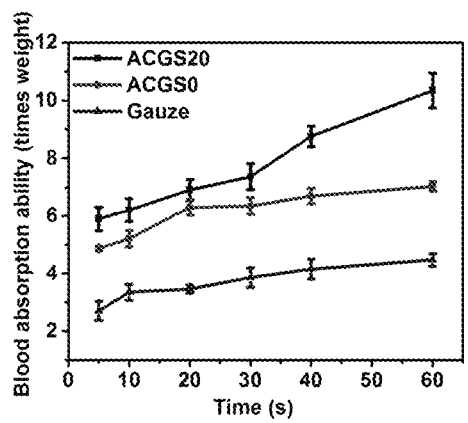
FIG. 5 is a contrast diagram showing the blood absorption capacity among dodecyl chitosan-graphene oxide composite sponge, dodecyl chitosan sponge and medical gauze.

It can be seen from FIG. 5 that the blood absorption capacity of the sponge is obviously superior to the medical gauze, in which, ACGS0 may absorb blood equivalent to 7 times its own weight within 60 s, and ACGS20 may absorb blood equivalent to 10 times its own weight within 60 s. If alkyl chitosan sponge and medical gauze are set as contrast examples, the alkyl chitosan-graphene oxide composite sponge provided by the present invention has significantly-improved blood absorption performance. The test results of other embodiments were the same as the test results of embodiment 11.

Figure 6:
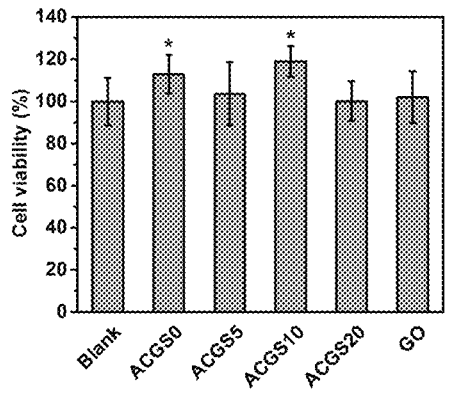
FIG. 6 is a contrast diagram showing the MRC5 cell viability statistics in an MTT cytotoxicity test among the blank sample, dodecyl chitosan sponge, dodecyl chitosan-graphene oxide composite sponge and graphene oxide powder.

In the present invention, the material cytotoxicity was tested by an MTT way (reference standard: GB16886.5-2017 Biological Evaluation of Medical Devices-Part 5: In-vitro cytotoxicity test), during test process, MRC5 cells were used as a model to characterize the biocompatibility of the composite sponge, and the test results were shown in FIG. 6. In FIG. 6, * represents that there is a significant difference relative to the blank group (p<0.05). It can be seen from the test results of FIG. 6 that alkyl chitosan sponge ACGS0 and composite sponge ACGS10 may promote MRC5 cells growth, and have a significant difference relative to the blank group; the acceleration of ACGS5, ACGS20 to MRC5 cells growth is equivalent to the blank group, indicating that the alkyl chitosan-graphene oxide composite sponge has excellent biocompatibility; the test results of the composite sponge obtained from other embodiments are slightly higher than that of the blank group, indicating that the composite sponge has good biocompatibility.

Figure 7:
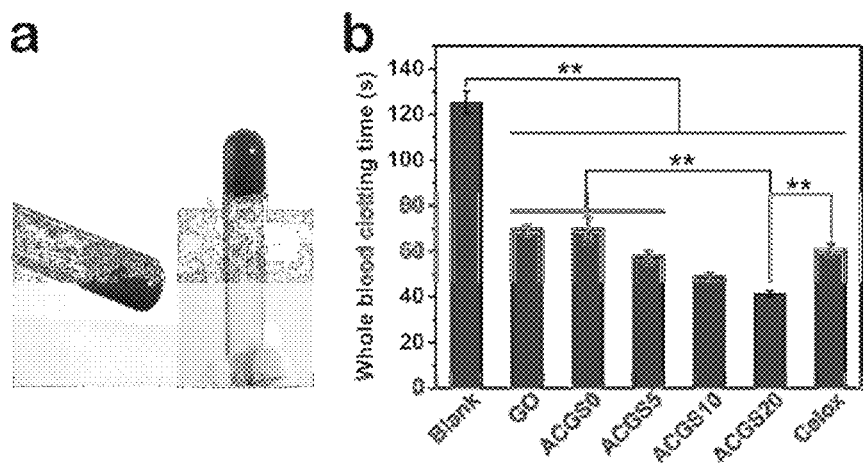
FIG. 7 is a contrast diagram showing the test results statistics of in-vitro whole blood coagulation time among a blank sample, graphene oxide powder, dodecyl chitosan sponge, dodecyl chitosan-graphene oxide composite sponge and Celox hemostatic powder.

In-vitro whole blood coagulation test (the method was the same as the test method of the whole blood coagulation time of the former alkyl chitosan): tested the time required by a mixture of ACGS20 and anti-coagulating whole blood to change from a flow condition into a gel condition capable of supporting its own weight via $CaCl_2$ activation, and the test results were shown in FIG. 7, in FIG. 7, (a) a contrast diagram of the mixture of ACGS20 and anti-coagulating whole blood before and after coagulation; (b) WBCT value (whole blood coagulation time) of Blank, GO, ACGS0, ACGS5, ACGS10, ACGS20 and Celox, ** indicates that there is a significant difference (p<0.01). It can be seen from the test results of FIG. 7 that ACGS20 has a shortest in-vitro whole blood coagulation time, about 41 s, and has the most excellent in-vitro blood coagulation effect.

Figure 8:
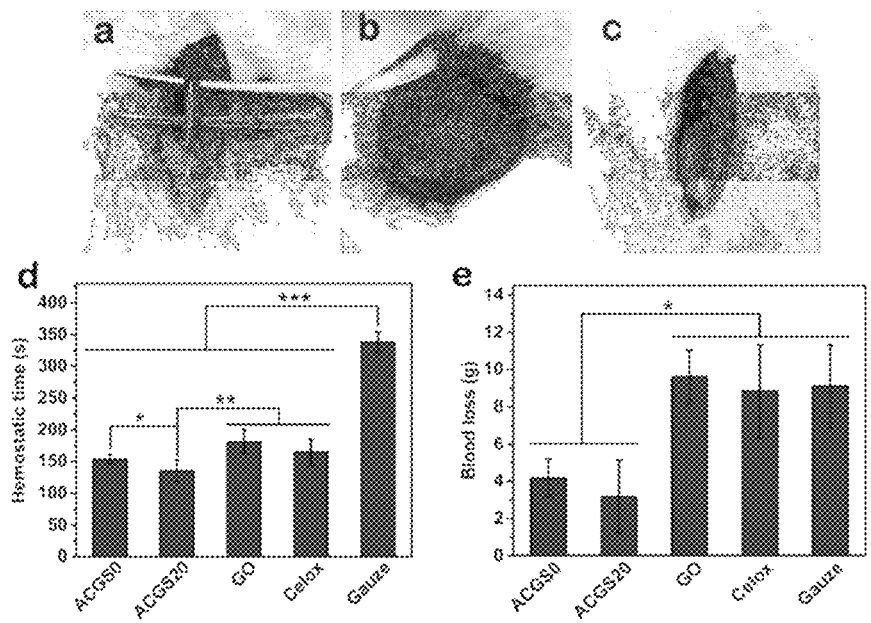
FIG. 8 is a contrast diagram showing the test results statistics in a rabbit femoral hemorrhage wound model test among dodecyl chitosan sponge, dodecyl chitosan-graphene oxide composite sponge, graphene oxide powder, Celox hemostatic powder and medical gauze.

A rabbit femoral artery hemorrhage model was used to evaluate the hemostasis of the alkyl chitosan-graphene oxide composite sponge, in this experiment, the products obtained from embodiments 4 and 11 were set as examples for testing. The specific test method was as follows: a healthy and grown male New Zealand rabbit was selected and its weight was controlled within 2.5±0.2 kg. Moreover, the artery and vein at the bottom of right thighbone of the rabbit was completely cut, the blood gushed out, as shown in FIG. 8(a). ACGS0 or ACGS20 (about 0.5 g) was covered on the surface of a wound, the operation of powdered materials is not so convenient as the sponge dressing, therefore, it required more powder, the wound may be completely covered by about 2 g GO and Celox here. Moreover, ACGS0, ACGS20 and Celox may tightly adhere on the surface of the wound and may rapidly seal the bleeding wound, the test results were shown in FIG. 8, in FIG. 8, (a) the artery and vein at the bottom of the rabbit's thighbone was exposed; (b) the bleeding wound was covered by ACGS20; (c) ACGS20 was taken out from the wound after successful hemostasis; (d) the hemostasis time of ACGS0, ACGS20, GO, Celox and Gauze group; (e) the hemorrhage mass of ACGS0, ACGS20, GO, Celox and Gauze group; * indicates that there is a significant difference (p<0.05),  indicates that there is a very significant difference (p<0.01), * indicates that there is a remarkably significant difference (p<0.001). It can be seen from FIG. 8 that ACGS20 hemostasis time (134.64±17.10 s) is shorter than that of ACGS0 (153.07±7.33 s) or GO (181.25±19.37 s), and the hemorrhage mass (3.17±1.96 g) is less than that of ACGS0 (4.20±1.93 g) or GO (9.61±1.44 g).

It can be seen from the above embodiments that the alkyl chitosan-graphene oxide composite sponge provided by the present invention has a pore structure and has good blood absorption capacity, moreover, the coordination of alkyl chitosan and graphene oxide shortens the hemostasis time. The sponge material composed by alkyl chitosan and graphene oxide has excellent hemostasis capacity and is expected to be a novel hemostatic material for promotion.

Although the aforementioned embodiments illustrate the present invention in detail, they are only parts of the embodiments of the present invention, rather than all of the embodiments. Other embodiments can be obtained by people according to these embodiments without the premise of inventiveness, and all of the embodiments fall within the claimed scope of the present invention.

What is claimed is:

1. An alkyl chitosan-graphene oxide composite sponge wherein the absorbing capacity of the graphene oxide is 3-28 wt. %.

2. The alkyl chitosan-graphene oxide composite sponge according to claim 1, wherein the alkyl chitosan-graphene oxide composite sponge has pores, and the porosity is 48-78%; the specific surface area of the alkyl chitosan-graphene oxide composite sponge is ≥100 $m^2/g$.

3. The alkyl chitosan-graphene oxide composite sponge according to claim 1, wherein the degree of alkyl substitution of the alkyl chitosan is 3-35%.

4. The alkyl chitosan-graphene oxide composite sponge according to claim 1, wherein the carbon chain of the grafted alkyl in the alkyl chitosan is C6-C18.

5. The alkyl chitosan-graphene oxide composite sponge according to claim 2, wherein the carbon chain of the grafted alkyl in the alkyl chitosan is C6-C18.

6. The alkyl chitosan-graphene oxide composite sponge according to claim 3, wherein the carbon chain of the grafted alkyl in the alkyl chitosan is C6-C18.

7. A preparation method of the alkyl chitosan-graphene oxide composite sponge according to claim 1, comprising the following steps of:
   (1) mixing a chitosan solution with aldehyde compounds, then adding a reducing agent to obtain alkyl chitosan after reaction;
   (2) mixing the alkyl chitosan with acetic acid, graphene oxide and water, then freeze-drying above mixed liquor to obtain an alkyl chitosan-graphene oxide composite sponge.

8. The preparation method according to claim 7, wherein in the step (1), the chitosan solution comprises chitosan, acetic acid, ethyl alcohol and water, and the mass ratio of the chitosan to water is 1:(80-120);
the mass ratio of the acetic acid to water is (0.8-1.2):100;
the volume ratio of the ethyl alcohol to water is (70-80):200.

9. The preparation method according to claim 7, wherein in the step (2), the dosage ratio of the alkyl chitosan to acetic acid is 0.1 g:(0.08-0.15) mL.

10. The preparation method according to claim 7, wherein in the step (1), the molar ratio of the aldehyde compounds to aminos in chitosan is (0.3-1.5):1.

11. The preparation method according to claim 9, wherein in the step (1), the molar ratio of the aldehyde compounds to aminos in chitosan is (0.3-1.5):1.

12. The preparation method according to claim 7, wherein the freeze drying temperature is −75 to −80° C., and the time is 45-50 h.

* * * * *